(12) United States Patent
Shelke

(10) Patent No.: US 8,518,048 B2
(45) Date of Patent: Aug. 27, 2013

(54) SAW CAPTURE DEVICE

(75) Inventor: Rajesh Tulsiram Shelke, Bangalore (IN)

(73) Assignee: Depuy International Limited (GB)

( * ) Notice: Subject to any disclaimer, the term of this patent is extended or adjusted under 35 U.S.C. 154(b) by 0 days.

(21) Appl. No.: 13/142,863

(22) PCT Filed: Jan. 7, 2010

(86) PCT No.: PCT/GB2010/050017
§ 371 (c)(1),
(2), (4) Date: Oct. 24, 2011

(87) PCT Pub. No.: WO2010/079356
PCT Pub. Date: Jul. 15, 2010

(65) Prior Publication Data
US 2012/0172879 A1 Jul. 5, 2012

(30) Foreign Application Priority Data
Jan. 7, 2009 (GB) .................................. 0900084.5

(51) Int. Cl.
*A61B 17/56* (2006.01)
(52) U.S. Cl.
USPC .............................................. 606/87; 606/88
(58) Field of Classification Search
USPC ..................... 606/86 R, 87, 88, 96
See application file for complete search history.

(56) References Cited

U.S. PATENT DOCUMENTS

| | | | | |
|---|---|---|---|---|
| 4,952,213 | A | * | 8/1990 | Bowman et al. ................. 606/79 |
| 5,207,680 | A | * | 5/1993 | Dietz et al. ................... 606/86 R |
| 2005/0171545 | A1 | * | 8/2005 | Walsh et al. .................... 606/72 |
| 2008/0262500 | A1 | | 10/2008 | Collazo |

FOREIGN PATENT DOCUMENTS

| | | |
|---|---|---|
| EP | 337901 A1 | 10/1989 |
| EP | 1430842 A1 | 6/2004 |
| GB | 2447702 A | 9/2008 |

OTHER PUBLICATIONS

PCT International Search Report and Written Opinion PCT/GB2010/050017 dated Jul. 27, 2010.
UK Search Report GB0900084.5 dated Apr. 29, 2009.

* cited by examiner

*Primary Examiner* — Kevin T Truong
*Assistant Examiner* — Christian Sevilla

(57) ABSTRACT

A saw capture device comprising a body (2), coupling means for coupling the body (2) to a cutting block (4), the cutting block (4) being arranged to couple to a bone and an adjustable guide (22) comprising at least one curved arm couplable to the body (2). The adjustable guide (22) is couplable to the body (2) in a first configuration in which the at least one arm is arranged in use to curve away from a bone and a second configuration in which the at least one arm in use is arranged to curve towards the bone. When coupled to a cutting block (4) the adjustable guide (22) is spaced apart from the cutting block (4) to define a cutting slot (18).

11 Claims, 5 Drawing Sheets

SAW CAPTURE DEVICE

CROSS REFERENCE TO RELATED APPLICATION

This application is a National Stage 35 U.S.C. 371 application of International Patent Application PCT/GB2010/050017 filed Jan. 7, 2010.

BACKGROUND OF THE INVENTION

The present invention relates to a saw capture device. In particular, the present invention relates to a saw capture device couplable to a cutting block in order to guide a surgical cutting tool to resect a bone.

During orthopaedic surgery it is commonly necessary to resect a portion of a bone, in particular an end of the bone. For instance, during a total knee replacement procedure, it is necessary to resect the ends of the tibia and femur about the knee joint. There are similar requirements for resecting other bones for instance at a hip or a shoulder joint for the implantation of other prosthetic devices. In order to perform the resection, a cutting instrument, for instance an oscillating saw blade, is guided by a surgeon along a predetermined resection plane.

When performing a resection of a bone it is important to ensure that the resection occurs accurately along the predetermined resection plane in order to ensure that the implanted prosthesis is not misaligned. It is known to provide a cutting block, which is couplable to the bone, providing a permanent slot through which the surgeon passes the blade of the cutting instrument. The slot is aligned with the predetermined resection plane and the cutting block coupled to the bone, for instance by temporarily fixing to the bone with pins.

Alternative cutting blocks include a saw capture device that is attached to the cutting block. A side of the cutting block comprises a first guide surface and a side of the saw capture device facing the cutting block comprises a second spaced apart guide surface. The blade of the cutting instrument is captured between the side of the cutting block and the saw capture device. It is known for the saw capture device to be removable from the cutting block, for instance using pegs or pins. Removable saw capture devices are disclosed in U.S. Pat. No. 5,693,056 and U.S. Pat. No. 5,611,802. The saw capture device of U.S. Pat. No. 5,611,802 comprises interchangeable arms of different sizes arranged to wrap around bones of different diameters, which further improves the alignment of the cutting instrument, and so the accuracy of the resection. Advantageously, providing a removable saw capture device allows the saw capture device to be removed for cleaning the cutting block.

It can be necessary to perform resections of bones having different shapes and diameters. Furthermore, the resection may be performed using different surgical approaches, for instance anterior-posterior cuts, distal femoral cuts and proximal tibial cuts. Each type of resection typically requires a different form of cutting block, both to allow the block to couple effectively to the bone and also to allow the profile of the cutting block to closely conform to the bone. Providing a dedicated saw capture device for each form of cutting block requires a large number of separate surgical instruments to perform resections of a full range of bones.

It is an object of embodiments of the present invention to obviate or mitigate one or more of the problems associated with the prior art, whether identified herein or elsewhere.

BRIEF SUMMARY OF THE INVENTION

According to a first aspect of the present invention there is provided a saw capture device comprising: a body; coupling means for coupling the body to a cutting block, the cutting block being arranged to couple to a bone; and an adjustable guide comprising at least one curved arm couplable to the body; wherein the adjustable guide is couplable to the body in a first configuration in which the at least one arm is arranged in use to curve away from a bone and a second configuration in which the at least one arm in use is arranged to curve towards the bone; and wherein when coupled to a cutting block the adjustable guide is spaced apart from the cutting block to define a cutting slot.

An advantage of the first aspect of the present invention is that the adjustable guide allows the saw capture device to accommodate the profile of different bones, or different portions of a single bone by moving the guide between the first configuration and the second configuration. Advantageously, allowing for a saw capture device to more closely conform to the profile of a bone reduces the risk of a misaligned saw cut. Furthermore, a single saw capture device may be coupled to a range of different cutting blocks to perform different resection procedures.

The adjustable guide may comprise first and second curved arms couplable to the body portion The saw capture device may further comprise a spacer coupled to the body for spacing the body and the adjustable guide apart from a cutting guide surface of a cutting block to define the height of the cutting slot.

The or each curved arm of the adjustable guide may comprise first and second guide surfaces such that in the first configuration the first guide surface is arranged to face the cutting block and in the second configuration the second guide surface is arranged to face the cutting block to define a side of the cutting slot.

The arms of the adjustable guide may extend from opposite sides of the body portion.

The body may comprise an upper body portion arranged to overlie a cutting guide surface of a cutting block and a side body portion extending from the upper body portion around a side of a cutting block, wherein the adjustable guide is couplable to the upper body portion. An end of the upper body portion remote from the side body portion may comprise a pin arranged to engage a hole extending through the adjustable guide to couple the adjustable guide to the body, wherein the adjustable guide may be moveable from the first configuration to the second configuration by removing the adjustable guide from the pin, rotating the adjustable guide through 180° about an axis which is orthogonal to the axis of the pin and reengaging the adjustable guide on the pin.

The upper body portion may further comprise a shelf portion arranged to contact the adjustable guide when the adjustable guide is engaged upon the pin such that the adjustable guide is prevented from rotating about the pin.

The saw capture device may further comprise a releasable latch pivotally coupled to the upper body portion arranged to extend over the adjustable guide to prevent the adjustable guide from being removed from the pin.

The saw capture device may further comprise a fixed guide comprising a pair of arms extending from opposite sides of the body portion, each arm comprising a cutting guide surface arranged such that when coupled to a cutting block the cutting guide surfaces of the fixed guide further define the cutting slot.

The coupling means may comprise a pin extending from the body portion arranged to engage a corresponding hole within a cutting block and a releasable catch moveable in direction transverse to the axis of the pin arranged to engage a notch within a surface of the cutting block. The releasable catch may be coupled to a button, the button in turn being coupled to the body and resilient biased such that the releasable catch is biased to engage the notch within a surface of the cutting block.

According to a second aspect of the present invention there is provided a cutting guide comprising: a cutting block couplable to a bone; and a saw capture device as described above arranged to couple to the cutting block such the adjustable guide is spaced apart from the cutting block to define a cutting slot.

According to third aspect of the present invention there is provided an instrument kit comprising: a femoral cutting block couplable to a femur, the femoral cutting block having a straight edge arranged to face a surface of a femur; a tibial cutting block couplable to a tibia, the tibial cutting block having a curved edge arranged to face and partially surround a surface of a tibia; and a saw capture device as described above arranged to couple to either cutting block such the adjustable guide is spaced apart from the cutting block to define a cutting slot. When the saw capture device is coupled to the femoral cutting block and the adjustable guide is in the first configuration a straight edge of the adjustable guide may extend generally parallel to an edge of the cutting block arranged to face a femur and when the saw capture device is coupled to the tibial cutting block and the adjustable guide is in the second configuration a curved edge of the adjustable guide may extend generally parallel to an edge of the cutting block arranged to face a tibia.

BRIEF DESCRIPTION OF THE DRAWINGS

The present invention will now be described, by way of example only, with reference to the accompanying drawings, in which.

DETAILED DESCRIPTION OF THE INVENTION

Figure 1:
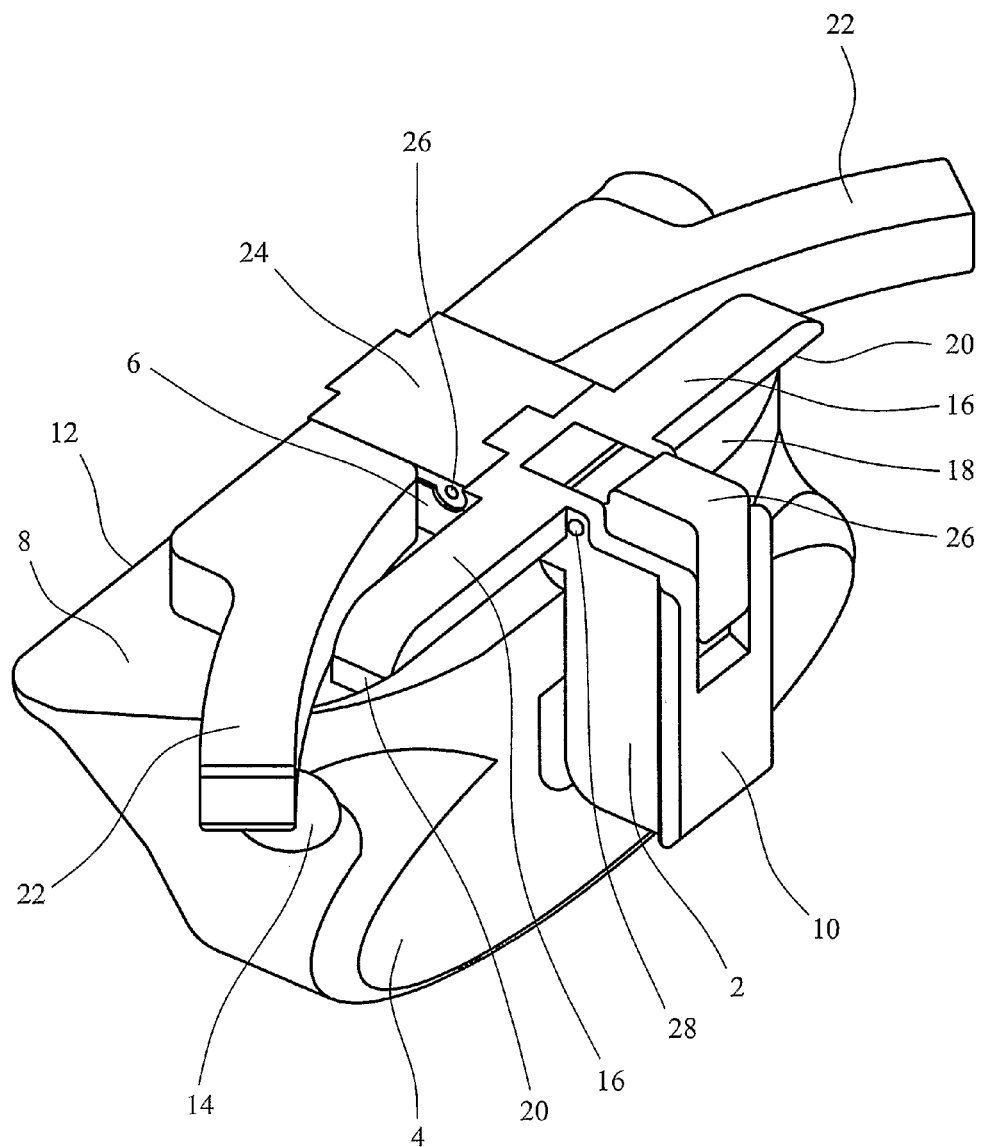
FIG. 1 illustrates a saw capture device in accordance with an embodiment of the present invention in a first configuration coupled to a first cutting block.

Referring first to FIG. 1 this illustrates a saw capture device in accordance with an embodiment of the present invention coupled to a first cutting block 4 for resecting a femur. The saw capture device comprises a body 2. The body 2 is provided with coupling means (not wholly visible in FIG. 1) for coupling to a cutting block 4. The body 2 comprises an upper body part 6 extending parallel to a cutting guide surface 8 of the cutting block 4 and a side body part 10 which overlaps the side of the cutting block 4. Cutting block 4 is arranged to couple to a bone such that a first edge 12 faces or is in contact with the bone. For instance, once correctly positioned, pins may be passed through fixation holes 14 into the bone such that the cutting block 4 provides a secure cutting platform for resecting the bone.

The saw capture device further comprises a fixed guide 16 comprising a pair of arms extending perpendicularly from the body portion 2. The saw capture device is arranged such that when the body 2 is coupled to a cutting block 4, the arms of the fixed guide 16 are spaced apart from the cutting block 4 to define a cutting slot 18. Cutting slot 18 is sized to receive a blade of cutting tool such that the blade is confined to cut the bone along a predetermined resection plane. The opening to cutting slot 18 defined by the fixed guide 16 incorporates a chamfer 20 to assist in inserting the cutting blade. Part or all of the upper body part 6 overlying the top of the cutting block 4 may also be spaced apart from the cutting block 4 such that the cutting slot 18 extends under the upper body part 6.

The saw capture device further comprises an adjustable guide 22 comprising a pair of curved arms extending from the body portion 2. The adjustable guide portion 22 comprises a substantially straight side and a curved side. The arms of the adjustable guide 22 are also spaced apart from the cutting block 4 to define the portion of the cutting slot 18 extending under the adjustable guide 22. The adjustable guide 22 is coupled to the body 2 such that it can be moved between a first configuration, as shown in FIG. 1, in which the arms curve away from the bone (such that a straight edge faces the bone) and a second configuration in which the arms curve towards the bone (such that a curved edge faces the bone). The adjustable guide 22 is secured to the body 2 via a latch 24, which is itself pivotally coupled to the body 2 by pivot pin 26. The coupling between the adjustable guide 22 and the body 2 will be described in greater detail below in connection with FIGS. 2 to 4.

The coupling means for coupling the body 2 to a cutting block 4 is arranged to positively engage the cutting block 4 such that the saw capture device cannot be displaced by vibration or force applied to a cutting blade within cutting slot 18. The coupling means can be released by pressing button 26, which is pivotally coupled to the body 2 by pivot pin 28. The coupling means is described below in greater detail with reference to FIG. 5.

Figure 2:
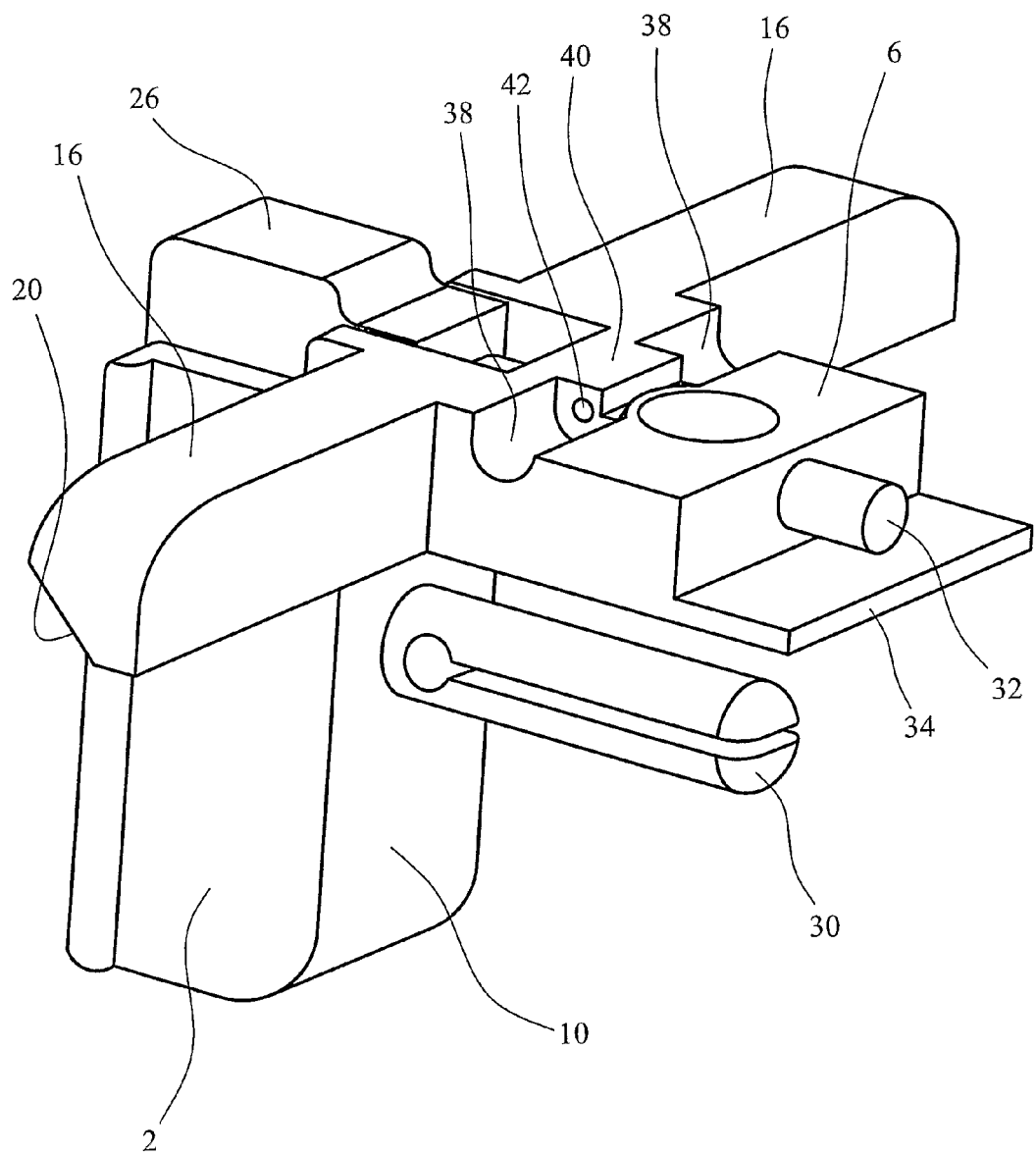
FIG. 2 illustrates part of the saw capture device of FIG. 1 partially disassembled with an adjustable guide portion removed.

Referring now to FIG. 2, this illustrates part of the saw capture device of FIG. 1 partially disassembled and removed from the cutting block 4. Coupling pin 30 extends from part 10 of the body 2 and forms part of the coupling means for coupling to the cutting block 4, as will be described below in greater detail with reference to FIG. 5. The adjustable guide 22 has been removed to illustrate how it couples to part 6 of the body 2. The upper body part 6 comprises a generally flat underside to define a cutting guide surface spaced apart in use from the cutting guide surface 8 of the cutting block 4 to define the cutting slot 18 there between. The end of the body 2 which in use faces towards the bone terminates in a pin 32 and a shelf 34. The pin 32 is arranged to engage a corresponding hole within the adjustable guide 22 and the shelf is arranged to press against a side of the adjustable guide 22 to prevent the guide rotating about the pin 32, as illustrate in FIG. 3.

Figure 3:
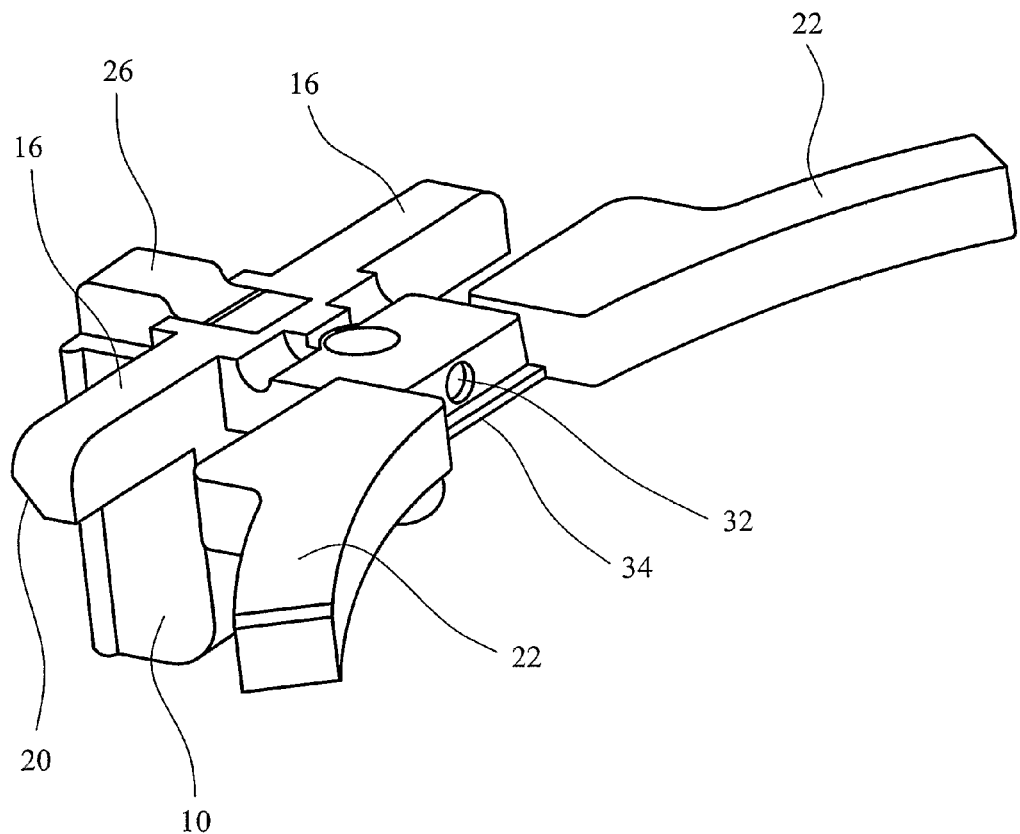
FIG. 3 illustrates part of the saw capture device of FIG. 1 partially disassembled and in a second configuration.

FIG. 3 shows the adjustable guide 22 coupled to the body 2 in a second configuration in which, in use, the arms of the adjustable guide are arranged to curve towards the bone and present a curved edge to the bone. In FIG. 3 the latch 24 has been removed to illustrate the coupling between the body 2 and the adjustable guide 22. Advantageously, the arms of adjustable guide 22 in the second configuration extend partly around the bone to allow for a more accurate resection. It will be appreciated that the adjustable guide may be moved between the first configuration and the second configuration by sling the adjustable guide 22 from pin 32, inverting the guide and reattaching to pin 32. Rotation about the pin 32 is prevented by shelf 34 which engages a side of the adjustable guide 22. The adjustable guide 22 comprises first and second cutting guide surfaces. When in either the first or the second configuration, a cutting guide surface is arranged to face the cutting guide surface 8 of a cutting block 4 to define the cutting slot 18. A central portion of the adjustable guide 22 about the hole for pin 32 is thinner than the arms so as to accommodate the shelf 34 such that a surface of the shelf 34 is contiguous with the cutting guide surface of the adjustable guide 22 facing the cutting block 4.

Figure 4:
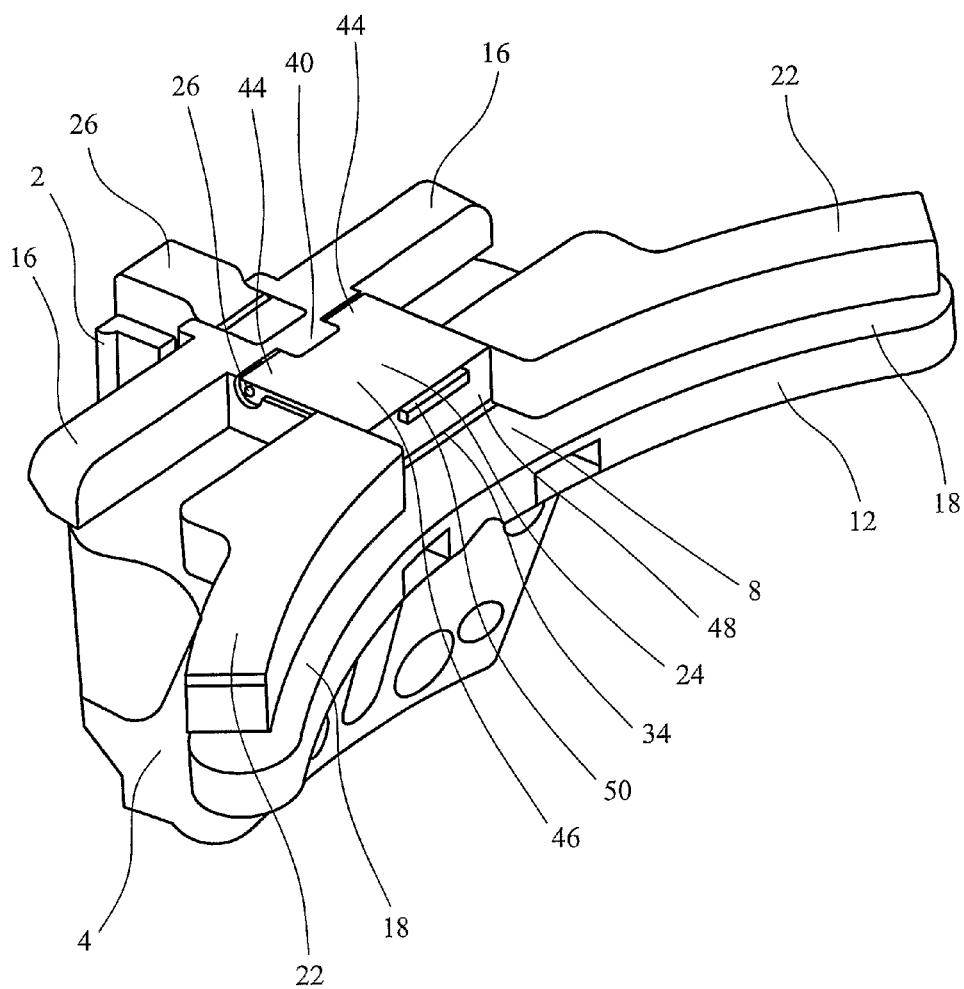
FIG. 4 illustrates the saw capture device of FIG. 1 in the second configuration coupled to a second cutting block.

FIGS. 2 and 3 further illustrate the upper surface of the upper body portion 6 further comprises hinge recesses 38 for coupling to the latch 24 and a hinge block 40 with a bore 42 to receive pivot pin 24. FIG. 4 illustrates the adjustable guide 22 coupled to the upper body portion 6 in the second configuration secured by latch 24. Latch 24 comprises hinge parts 44 secured to the upper body portion by pivot pin 26 which passes through the hinge parts 44 and bore 42 such that the hinge parts 44 can rotate within hinge recesses 38. Latch 24 further comprises an upper flap 46 which passes over the adjustable guide 22 and a front face 48 arranged wrap over the adjustable guide 22 to prevent the adjustable guide 22 from being removed from pin 32. An edge of front face 48 rests against shelf 34 such that the central portion of the adjustable guide 22 is completely surrounded. Latch 24 further comprises a tab 50 which can be manipulated to lift up the latch 24 by rotating about pivot pin 26 to release the adjustable guide portion 22.

FIG. 4 illustrates the saw capture device coupled to a tibial cutting block 4. The tibial cutting block 4 incorporates a curved front edge 12 arranged to extend partially around a tibia. When in the second configuration, the edge of the arms of the adjustable guide 22 facing the bone mirrors the cutting block front edge 12. By allowing the saw capture device to partially wrap around the tibia a more accurate resection may be achieved. Reducing the gap between the saw capture device and the bone around the sides of the bone reduces the potential for the cutting blade to bend or twist between the cutting slot 18 and the bone. For resecting bones having a different profile, the adjustable guide 22 may be coupled to the body 2 in the first configuration to prevent the arms of the adjustable guide impinging upon soft tissue surrounding the bone.

Figure 5:
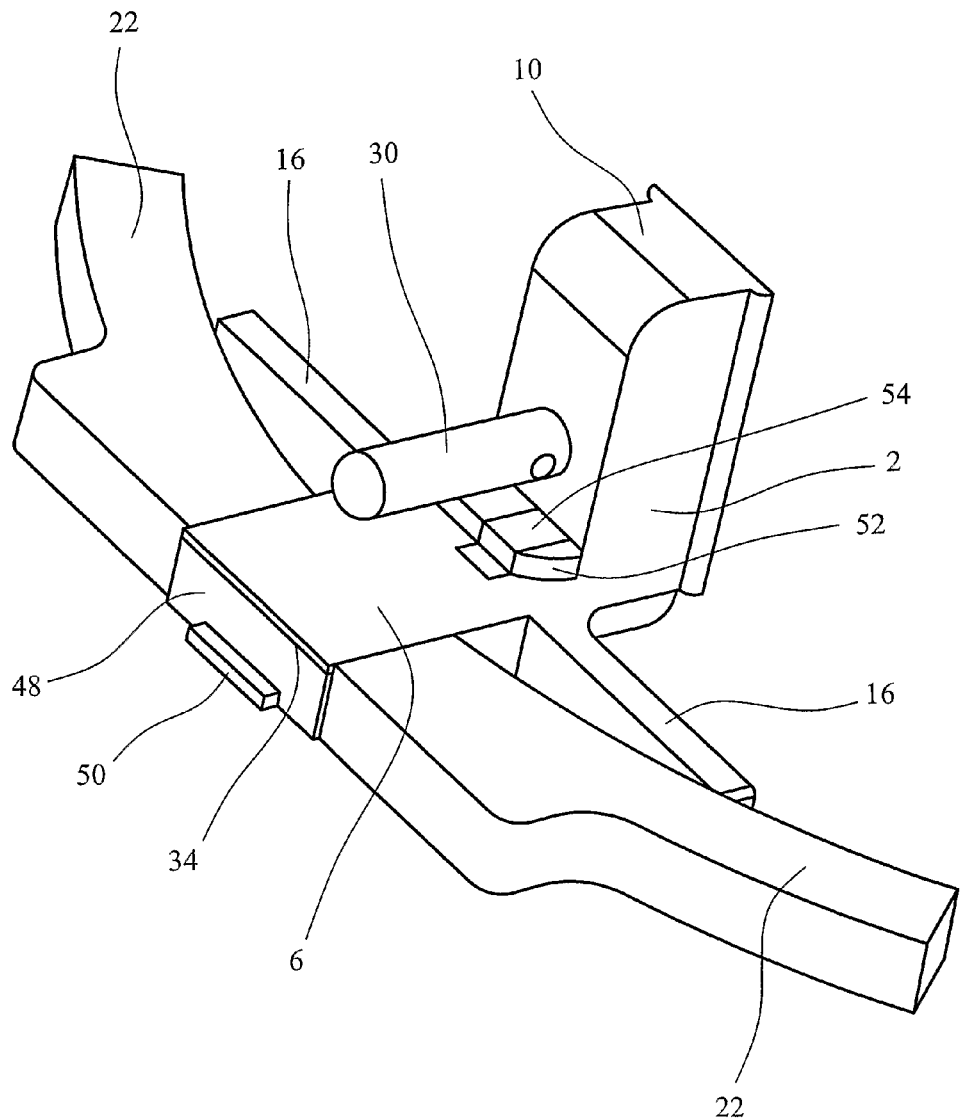
FIG. 5 illustrates the saw capture device of FIG. 1 in the first configuration decoupled from the cutting block.

Referring now to FIG. 5, this illustrates an assembled saw capture device viewed from below decoupled from a cutting block. It can be seen that the undersides of the upper body portion 6, the fixed guide 16 and the adjustable guide 22 define cutting surfaces lying within a single plane. The adjustable guide 22 comprises two cutting surfaces on opposite sides such that a cutting surface is provided facing the cutting block in both the first and the second configuration. When coupled to a cutting block, the upper body portion 6 (and therefore the fixed guide 16 and the adjustable guide 22) is spaced apart from cutting guide surface 8 of the cutting block by step portion 52, which forms part of body 2. The height of step portion 52 defines the size of the cutting slot 18.

FIG. 5 further illustrates the coupling means for coupling the body 2 to the cutting block 4. The coupling means comprises pin 30 which is arranged to be received within a corresponding hole in the side of the cutting block 4. Pin 30 is split into two halves which are compressible together to ease their insertion into the hole within cutting block 4. The coupling means further comprises a releasable tab 54 arranged to engage a corresponding notch upon the upper surface of the cutting block 4. Tab 54 is coupled to button 26, which is spring loaded such that the tab 54 is normally biased to engage the notched cutting guide. To release the saw capture device from the cutting block, button 26 is depressed causing the button and the tab 54 to pivot about pivot pin 28 releasing the tab 54 from the notched cutting block surface. The saw capture device can then be removed by sliding pin 30 from the hole within the cutting block.

As described above, each saw capture comprises a fixed guide portion and an adjustable guide portion. It will be appreciated that in certain embodiments of the present invention there may be no fixed guide portion. Furthermore, the saw capture device may be provided in a range of sizes suitable to fit different cutting blocks and bones. Alternatively, the saw capture device may be provided with a single body portion and two or more adjustable guide portions, for which the adjustable guide portions may have different length arms, or arms having a different curvature, optimised to conform to different size bones. Furthermore, in certain embodiments of the present invention, the adjustable guide portion may comprise only a single curved arm (optionally, with an accompanying straight arm). When coupled to a cutting block having a straight edge facing the bone, it is preferable to couple the adjustable guide to the body such that a straight edge of the guide faces the bone, thereby mirroring the shape of the cutting block. For performing a proximal resection of a tibia, it is preferable to use a cutting block having a curved edge facing the bone as the proximal part of the tibia is substantially broader than the remainder of the bone. By using a curved cutting block, together with a saw capture device in the second configuration, the cutting slot extends closer to the bone, which reduces the risk of the saw blade deviating from the required resection plane.

Further modifications to, and applications of, the present invention will be readily apparent to the appropriately skilled person from the teaching herein, without departing from the scope of the appended claims.

The invention claimed is:

1. A cutting guide device for use with a bone, comprising:
a cutting block having a first side and a cutting block surface, the cutting block being couplable to the bone such that the first side faces away from the bone;
a body releasably coupled to the cutting block and comprising an upper body part and a side body part extending from the upper body part, the body being configured such that, when the body is coupled to the cutting block, the side body part is disposed adjacent the first side of the cutting block; and
an adjustable guide comprising at least one curved arm releasably coupled to the upper body part in a first configuration, whereat the at least one curved arm is curved towards the side body part and away from the bone when the cutting block is coupled to the bone, and in a second configuration, whereat the at least one curved arm is curved away from the side body part and towards the bone when the cutting block is coupled to the bone;
wherein the upper body part comprises a generally flat underside and, when the adjustable guide is coupled to the upper body part in the first configuration and the second configuration, the at least one curved arm defines a surface that is substantially contiguous with the underside of the upper body part to define together a cutting guide surface arranged to extend parallel to the cutting block surface to define a cutting slot that extends to the first side of the cutting block.

2. The cutting guide device of claim 1, wherein the adjustable guide comprises a first curved arm and a second curved arm.

3. The cutting guide device of claim 1, wherein the at least one curved arm of the adjustable guide comprises a first guide surface and a second guide surface, and wherein, when the adjustable guide is coupled to the upper body part in the first configuration, the first guide surface is arranged to face the cutting block, and when the adjustable guide is coupled to the upper body part in the second configuration, the second guide surface is arranged to face the cutting block.

4. The cutting guide device of claim 2, wherein the first arm and the second arm of the adjustable guide extend in opposite directions when the adjustable guide is coupled to the upper body part.

5. The cutting guide device of claim 1, wherein the upper body part comprises a first pin and the adjustable guide has a hole arranged to receive the first pin to thereby couple the adjustable guide to the body, and wherein the adjustable guide is moveable from the first configuration to the second configuration by removing the adjustable guide from the first pin, rotating the adjustable guide 180° about an axis that is orthogonal to the axis of the first pin and reengaging the adjustable guide on the first pin.

6. The cutting guide device of claim 5, wherein the upper body part further comprises a shelf portion that prevents the adjustable guide from rotating about the first pin when the adjustable guide is coupled to the upper body part.

7. The cutting guide device of claim 5, further comprising a releasable latch pivotally coupled to the upper body part, the latch being pivotable from a first position, wherein the adjustable guide may be released from the upper body part, and a second position, wherein the adjustable guide prevents the adjustable guide from being released from the upper body part.

8. The cutting guide device of claim 1, further comprising a fixed guide comprising a pair of arms extending in opposite directions from the upper body part, each arm having a cutting surface arranged such that, when the body is coupled to a cutting block, the cutting surfaces of the fixed guide and the cutting block surface define a portion of the cutting slot.

9. The cutting guide device of claim 1, wherein the side body part comprises a second pin extending therefrom and the cutting block has a hole sized to receive the second pin.

10. An instrument kit, comprising:
a femoral cutting block couplable to a femur, the femoral cutting block having a femoral cutting block surface and a straight edge arranged to face a surface of a femur;
a tibial cutting block couplable to a tibia, the tibial cutting block having a tibial cutting block surface a curved edge arranged to face and partially surround a surface of a tibia; and
a body releasably coupled to one of the femoral cutting block and the tibial cutting block, the body comprising an upper body part and a side body part extending from the upper body part; and
an adjustable guide comprising at least one curved arm releasably coupled to the upper body part in a first configuration, whereat the at least one curved arm is curved towards the side body part, and in a second configuration, whereat the at least one curved arm is curved away from the side body part;
wherein the upper body part comprises a generally flat underside and, when the adjustable guide is coupled to the upper body part in the first configuration and the second configuration, the at least one curved arm defines a surface that is substantially contiguous with the underside of the upper body part to define together a cutting guide surface that extends parallel to one of the femoral cutting block surface and the tibial cutting block surface to define a cutting slot that extends to the first side of one of the femoral cutting block surface and the tibial cutting block.

11. An instrument kit according to claim 10, wherein, when the body is coupled to the femoral cutting block and the adjustable guide is in the first configuration, a straight edge of the adjustable guide extends generally parallel to an edge of the cutting block arranged to face a femur, and when the saw capture device is coupled to the tibial cutting block and the adjustable guide is in the second configuration, a curved edge of the adjustable guide extends generally parallel to an edge of the cutting block arranged to face a tibia.

* * * * *